(12) United States Patent
Smith et al.

(10) Patent No.: US 12,714,596 B2
(45) Date of Patent: Aug. 25, 2026

(54) THERMALLY CONTROLLED FACE ENGAGING DEVICE

(71) Applicant: EMBR Labs IP LLC, Boston, MA (US)

(72) Inventors: Matthew J. Smith, Somerville, MA (US); Locklin George, Boston, MA (US)

(73) Assignee: EMBR Labs IP LLC, Boston, MA (US)

( * ) Notice: Subject to any disclaimer, the term of this patent is extended or adjusted under 35 U.S.C. 154(b) by 925 days.

(21) Appl. No.: 18/010,023

(22) PCT Filed: Jun. 11, 2021

(86) PCT No.: PCT/US2021/036955
§ 371 (c)(1),
(2) Date: Dec. 13, 2022

(87) PCT Pub. No.: WO2021/257394
PCT Pub. Date: Dec. 23, 2021

(65) Prior Publication Data

US 2023/0226365 A1 Jul. 20, 2023

Related U.S. Application Data

(60) Provisional application No. 63/041,734, filed on Jun. 19, 2020.

(51) Int. Cl.
*A61F 7/00* (2006.01)
*A61M 16/10* (2006.01)

(52) U.S. Cl.
CPC ......... *A61F 7/007* (2013.01); *A61M 16/1075* (2013.01); *A61F 2007/0075* (2013.01)

(58) Field of Classification Search
CPC .. A61F 7/007; A61F 2007/0075; A62B 9/003; A61M 16/1095; A61M 16/1075
See application file for complete search history.

(56) References Cited

U.S. PATENT DOCUMENTS 6,119,684 A 9/2000 Nohl et al.
8,702,775 B2 * 4/2014 Dunbar .................. A61F 7/007 607/108

(Continued)

OTHER PUBLICATIONS

International Search Report and Written Opinion mailed Sep. 2, 2021 in connection with International Application No. PCT/US2021/036955.

*Primary Examiner* — Kaitlyn E Smith
(74) *Attorney, Agent, or Firm* — Wolf, Greenfield & Sacks, P.C.

(57) ABSTRACT

A face engaging device such as a nozzle, facemask, etc., may include a housing including a fluid channel extending through the housing to an opening configured to be placed in fluid communication with the mouth of a user. The housing may include a first surface configured to be placed in contact with the skin of the user and a second surface exposed to the fluid channel. The face engaging device may also include a thermal actuator supported by the housing and including a first heat transfer surface position on the first surface, where the first heat transfer surface is configured to apply a thermal profile to the skin of the user when the opening is placed in fluid communication with the mouth of the user.

24 Claims, 6 Drawing Sheets

(56) References Cited

U.S. PATENT DOCUMENTS

| | | | | |
|---|---|---|---|---|
| 11,364,143 | B2 * | 6/2022 | Draper | A61F 7/0085 |
| 2013/0327323 | A1 | 12/2013 | Rubin | |
| 2014/0000626 | A1 * | 1/2014 | O'Connor | A61M 16/0875<br>128/207.18 |
| 2014/0261486 | A1 | 9/2014 | Potter et al. | |
| 2015/0150308 | A1 | 6/2015 | Monsees et al. | |
| 2017/0216539 | A1 | 8/2017 | Huber et al. | |
| 2017/0259088 | A1 * | 9/2017 | Garafolo | A62B 18/045 |

* cited by examiner

THERMALLY CONTROLLED FACE ENGAGING DEVICE

RELATED APPLICATIONS

This application is a National Stage filing under 35 U.S.C. § 371 of International Patent Application Serial No. PCT/US2021/036955, filed Jun. 11, 2021, which claims the benefit of priority under 35 U.S.C. § 119(e) of U.S. Provisional Application Ser. No. 63/041,734, filed Jun. 19, 2020. The entire contents of these applications are incorporated herein by reference in its their entirety.

FIELD

Disclosed embodiments are related to thermally controlled face engaging devices and related methods of use.

BACKGROUND

Wearable technology has become of great interest, enabled by the shrinking of sophisticated microelectronics, maturation of wireless communication, and increasing energy density of various battery chemistries. However, wearable technology to date has focused primarily on sensing and data collection. Haptic actuation, and in particular the generation of thermal sensations, has been increasingly recognized as an impactful area for mobile technology. Specifically, thermoelectric systems have been of great interest for applying cooling to the human body. Also, improving battery capacity has made it possible to integrate electronic devices such as thermoelectric systems into mobile technology. Thermoelectric systems offer several advantages in such applications including small form factors (especially compared with compressor technology), no moving parts which may be mechanically robust and silent, and precise dynamic control over thermal profiles applied by the system.

SUMMARY

In some embodiments, a face engaging device includes a housing having a fluid channel extending through at least a portion of the housing to an opening configured to be placed in fluid communication with a mouth and/or nose of a user, where the housing includes a first surface configured to be placed in contact with a user's skin and a second surface exposed to the fluid channel. The face engaging device also includes a thermal actuator supported by the housing and including a first heat transfer surface positioned on the first surface, where the first heat transfer surface is configured to be in contact with the skin of the user when the opening is placed in fluid communication with the mouth and/or nose of the user, and where the thermal actuator includes a second heat transfer surface positioned on the second surface.

In some embodiments, a face engaging device includes a housing having a fluid channel extending through at least a portion of the housing to an opening configured to be placed in fluid communication with a mouth and/or nose of a user, where the housing includes a first surface configured to be placed in contact with a user's skin and a second surface exposed to the fluid channel. The face engaging device also includes a thermal actuator supported by the housing, where the thermal actuator is configured to apply a thermal profile to the skin of the user when the opening is placed in fluid communication with the mouth and/or nose of the user, and where the thermal actuator is configured to transfer heat between the thermal actuator and fluid disposed in the fluid channel.

In some embodiments, a method of operating a face engaging device including a thermal actuator includes placing an opening of a housing of the face engaging device in fluid communication with a mouth and/or nose of a user, where the opening is connected to a fluid channel extending through the housing, applying a thermal profile to the skin of the user with a thermal actuator supported by the housing when the opening is placed in fluid communication with the mouth and/or nose of the user, drawing fluid through the fluid channel and into the mouth of the user, and transferring heat between the thermal actuator and the fluid passing through the fluid channel.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1A:
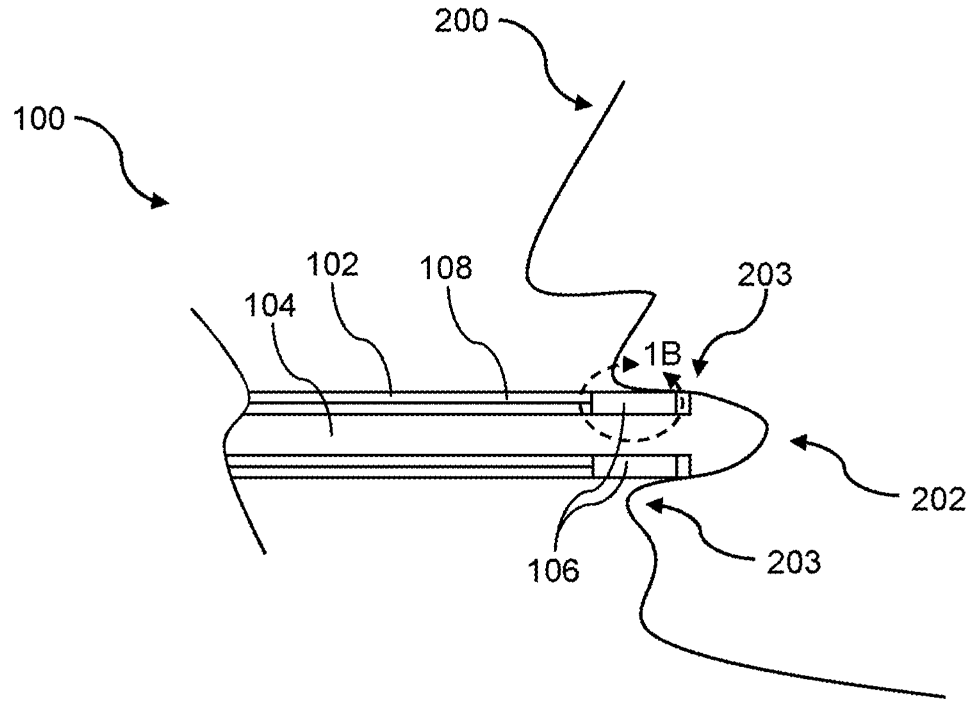
FIG. 1A is a schematic of one embodiment of a thermally controlled face engaging device in use by a user.

Conventional devices that apply thermal profiles to the skin are affected by thermoreceptor density on a portion of the body to which the thermal profile is applied. That is, thermoreceptor density may affect perceived temperature changes by a person. The mouth and face is an area of the body with high thermoreceptor density relative to other portions of the body. Additionally, the mouth is a part of the gustatory system, where subjective sensations may be a combination of taste and temperature, among other sensations.

In view of the above, the inventors have recognized the benefits of a face engaging device that includes a thermal actuator configured to apply a thermal profile to one or more portions of the mouth and/or face of a user. Thus, depending on the embodiment the face engaging device may be more specifically a mouth and/or nose engaging device that applies thermal sensations to one or more portions of a user's face including the lips, mouth interior, nose, and/or portions of the face surrounding these regions. For example, a face engaging device may be used to generate oral sensations, where temperature profiles are applied to the skin in combination with fluid passing into the mouth and/or nose. The face engaging device may provide subjective sensations of texture, taste, smell, chemical sensitivity (menthol, capsaicin), and/or combinations thereof in combination with temperature. The inventors have appreciated that thermal sensations can have a powerful effect on the overall experience of oral fluid delivery, and are often associated with pleasant and/or mood altering effects of the fluid.

Conventional devices that apply thermal profiles to skin typically employ large heat sinks or heat diffusion arrangements to allow for extended operation of the device without overheating a portion of the device or otherwise using energy inefficiently for active cooling. For example, some devices employ phase-change heat sinks, active fans, finned heat sinks, etc. However, such conventional arrangements may be bulky and/or energy intensive to operate.

In view of the above, the Inventors have recognized the benefits of a face engaging device that employs fluid moving through a fluid channel for waste heat dissipation. For example, in embodiments where a thermoelectric device (TED) is employed to apply a thermal profile to skin, one side of the thermoelectric device (or a thermally coupled surface) may be exposed to a fluid channel of a face engaging device. The act of the user generating a pressure differential in the mouth (e.g., inhaling, sucking, exhaling, and/or blowing) may draw fluid through the fluid channel. Alternatively, in some instances a pressured source (e.g. a pressurized gas tank) may force fluid to flow through the channel, as may occur in a scuba mouthpiece and/or facemask. In either case, this induced flow of fluid through the channel may transfer some of the heat from the thermoelectric device away from the face engaging device. In this manner, the face engaging device may transfer heat between the device and the flow of fluid to handle the thermal load generated during use of the device by a user.

According to exemplary embodiments described herein, the application of an adjustable, alternating thermal profile to the surface of human skin may interact with one or more physiological systems such that a physiological response is generated. For example, an adjustable alternating thermal profile may be used to modify one or more of vasoconstriction/vasodilation, respiration rate, heart rate, skin temperature, sweating, shivering, sympathetic response(s) (e.g., by the autonomic nervous system), perceived temperature on the skin, and/or thermal pleasure in a human subject (e.g., the user). Perceived temperature on the skin and thermal pleasure may be collectively referred herein as "subjective thermal sensations."

In some embodiments, a face engaging device includes a housing having an opening configured to be placed in fluid communication with the mouth and/or nose of a user. The housing may include a first surface configured to be placed in contact with the skin of the user (e.g., face, lips, mouth area, etc.) during use and a second surface exposed to the fluid channel. In some embodiments, the housing may be configured as a mouthpiece (e.g., a nozzle, straw, or similar structure) configured to fit at least partially within the mouth of the user, in which case the first surface may be an exterior surface and the second surface may be an interior surface of the housing. In some embodiments, the housing may be configured as a facemask, in which case both the first and second surfaces may be interior surfaces of the housing. The housing may take any suitable form that may allow a fluid channel to fluidly communicate with the mouth of a user when a surface of the housing is in contact with a user's skin, as the present disclosure is not so limited. The face engaging device may also include a thermal actuator supported by the housing and including a heat transfer surface configured to apply a thermal profile to the skin of the user when the fluid channel is in fluid communication with the user's mouth. In some embodiments, the thermal actuator is configured to transfer heat to fluid disposed in the fluid channel of the housing. For example, in some embodiments the thermal actuator may include a first heat transfer surface configured to be positioned on the skin of the user, and a second heat transfer surface positioned in contact with the fluid. Accordingly, when the thermal actuator is operated, waste heat may be transferred to fluid in the fluid channel to regulate the temperature of the thermal actuator. In some embodiments, the thermal actuator is configured to transfer heat from the fluid to the thermal actuator. For example, heat may be drawn from the fluid to regulate the temperature of the thermal actuator.

In some embodiments, a heat transfer surface of a thermal actuator positioned in the fluid channel may include texturing such as fins, pins, heat spreaders, etc. that improve convective heat transfer efficiency by increasing surface area of the heat transfer surface relative to a flat heat transfer surface. In some embodiments, the heat transfer surface of a thermal actuator positioned in the fluid channel may be larger than a heat transfer surface configured to be positioned against a user's skin. In some embodiments, heat transfer surfaces of a thermal actuator may be thermally coupled and/or include a heat spreader configured to provide heat transfer to an area larger than that of thermal actuating elements of the thermal actuator. According to such embodiments, the heat spreaders may be formed of a thermally conductive material so that heat transfer between the thermal actuator and an adjacent surface or fluid is not impeded. According to exemplary embodiments described herein, heat spreaders may be positioned on or integrated with a single heat transfer surface of a thermal actuator (e.g., interior or exterior surfaces), or may be positioned on or integrated with multiple heat transfer surfaces of a thermal actuator, as the present disclosure is not so limited. Thus, it should be understood that a thermal actuator may either be in direct thermal contact and/or indirect thermal contact, e.g.

through one or more of the above noted thermally conductive structures, with a fluid within a channel and/or a user's skin.

According to exemplary embodiments described herein, a face engaging device may include one or more thermal actuators configured to apply a thermal profile to a user's skin. In some embodiments, a thermal actuator may be configured as a thermoelectric device. The thermoelectric device may be employed to apply heating thermal profiles (e.g., where temperature is raised from an initial starting temperature) and/or cooling thermal profiles (e.g., where temperature is lowered from an initial starting temperature). In some embodiments, a first side of the thermoelectric device may be configured to be placed in contact with a user's skin, while a second, opposite side of the thermoelectric device may positioned in, or in thermal contact with a separate surface in, a fluid channel of the face engaging device. Such an arrangement may allow the heat output from the thermoelectric device to be regulated by fluid passing through the fluid channel. Of course, a thermoelectric device may have any suitable arrangement for heat transfer in a face engaging device, as the present disclosure is not so limited. In other embodiments, a thermal actuator may be configured as a resistive heater configured to provide heating thermal profiles to a user's skin. In such an embodiment, the thermal actuator may not be configured to transfer heat to the fluid path. However, in other embodiments the thermal actuator may transfer heat to fluid in a fluid channel of the face engaging device, as the present disclosure is not so limited. It should also be appreciated that any suitable thermal actuators may be employed in a face engaging device, as the present disclosure is not so limited.

According to exemplary embodiments described herein, a face engaging device includes a fluid channel though which a fluid may pass into the mouth of a user. That is, the fluid channel may be configured to be placed in fluid communication with a mouth of the user via an opening. In some embodiments, fluid flow through the fluid channel may be generated outside of the face engaging device. For example, a user may inhale or suck with the mouth to generate a pressure differential between the mouth and the external environment. In this example, the fluid channel may include an inlet through which environmental fluid (e.g., air or another gas, water or another liquid, etc.) may pass into the fluid channel and into the mouth of the user. In some embodiments, flow of fluid through the fluid channel may be powered. For example, in some embodiments, a pressurized source of gas or fluid may be coupled to the fluid channel and be selectively actuable to release or eject the gas or fluid into the fluid channel. In some embodiments, a face engaging device may include a fan, pump, or other powered actuator configured to drive fluid through the fluid channel. Accordingly, any suitable arrangement for moving fluid through a fluid channel of the face engaging device may be employed, as the present disclosure is not so limited.

According to exemplary embodiments described herein, a face engaging device may be employed on a variety of different devices configured to deliver various fluids to the mouth and/or nose of a user or receive various fluids from the mouth and/or nose of a user. Devices which may include a face engaging device include, but are not limited to, straws for drinks, inhalers, vaporizers, breathalyzers, gas masks, face masks, air supply masks, scuba masks, scuba mouthpieces, and/or any other appropriate device where a fluid (e.g. a gas and/or liquid) flows through a portion of the device to a user's mouth and/or nose. Fluids that may be delivered to the mouth and/or nose of a user via a face engaging device include, but are not limited to, a fluid from the external environment, aerosols, pressurized gas or liquids, vaporized chemicals, a flow of gas or liquid including entrained powders, ambient air, drinks, sensory-active chemicals (e.g., menthol, capsaicin, etc.), mood enhancing chemicals (e.g., nicotine, THC, CBD, oxytocin, nitrous oxide, etc.), and combinations of the forgoing. Face engaging devices may be employed in one or more applications including, but not limited to, enhancing situational awareness, providing indicators, enhancing mood, assisting addiction cessation, providing relaxation, providing thermal comfort, providing alertness, changing behavior, relaxing muscles, enhancing pleasantness of delivery of chemicals, and/or other appropriate applications.

In some embodiments, a face engaging device includes a power supply, a processor, and a thermal actuator. The power supply may be configured as a portable power supply like a battery, or may be another electric power source. The processor may be configured to executed processor readable instructions stored in memory that may be included in the face engaging device. The processor may be configured to control the thermal actuator. For example, the processor may control a voltage and/or amperage applied to the thermal actuator to correspondingly control the thermal profile applied to skin of a user. In some embodiments, the processor may be configured to switch the thermal actuator on and off (i.e. chopping) to control the applied thermal profiles. However, embodiments in which the processor is capable of applying a voltage and/or current with a variable magnitude to control operation of a thermal actuator are also contemplated. In some embodiments, the processor may receive inputs from one or more sensors. For example, in some embodiments the processor may receive inputs from a temperature sensor measuring the temperature of a heat transfer surface. As another example, the processor may receive inputs from a pressure sensor measuring the pressure of the fluid channel of the face engaging device. The inputs from the one or more sensors may allow the processor to control the thermal actuator using closed loop and/or open loop feedback depending on the desired type of operation. Of course, in some embodiments a face engaging device may not include a processor and may instead be manually controlled by a user input device, as will be discussed further below.

In some embodiments, a face engaging device may be at least partly controlled based on input from one or more input devices. For example, in some embodiments an input device may be coupled to a relay or switch between the power supply and a thermal actuator. In some embodiments, an input device may provide inputs to a processor configured to execute computer readable instructions stored in memory. The processor may use the inputs in feedback control and/or control of thermal actuators. For example, the processor may employ the inputs to turn on power to a thermal actuator. As another example, the processor may employ the inputs for closed-loop and/or open-loop control of a thermal profile. In some embodiments, a face engaging device may include a switch or a button, which a user may operate to turn on or off the thermal actuator. Other devices may be employed with a face engaging device that receives a user input, including, but not limited, graphical user interfaces and dials. In some embodiments, a face engaging device may include a pressure sensor configured to detect a pressure of a fluid channel of the mouth interface. The pressure sensor may be configured to detect a threshold pressure, a differential pressure between the fluid channel and an environmental pressure, and/or a change in pressure from an initial, baseline, or equilibrium value, or a rate of change of pressure. In this embodiment, a thermal actuator may be connected to a power supply (i.e., a thermal profile may be started) based on a detection of a threshold differential pressure, a threshold absolute pressure, and/or a transient change in pressure from a resting, baseline, or equilibrium value. In some embodiments, a face engaging device includes a flow sensor configured to detect flow through a fluid channel. Information from the flow sensor may be employed to connect a thermal actuator to a power supply (i.e., a thermal profile may be started), for example, when flow is increased through the fluid channel. Of course, any suitable input device may be employed with a face engaging device, as the present disclosure is not so limited. In some embodiments, various parameters of a thermal profile may be modified based on one or more inputs from one or more input devices. For example, in some embodiments, the magnitude of temperature change or power applied in a thermal profile may be based at least partly on the magnitude of an absolute pressure measures, or a pressure change from a baseline. Of course, any inputs may be employed to control or modify one or more parameters of a thermal profile, as the present disclosure is not so limited.

According to exemplary embodiment described herein, a face engaging device may apply a thermal profile to the skin (e.g. lips) of a user. In some embodiments, a thermal profile may be monotonic (i.e., constantly increasing or constantly decreasing). In some embodiments, a thermal profile may include a rise and hold, where temperature increases or decreases and then a constant temperature is held. In some embodiments, a thermal profile includes a plurality of thermal pulses, where each thermal pulse includes an increase in temperature and/or a decrease in temperature between two or more temperatures that the thermal profile cycles between. In some embodiments, a plurality of thermal pulses may be applied in succession. Of course, any suitable thermal profile may be employed with any number of different portions that either increase and/or decrease in temperature as the present disclosure is not so limited.

Methods and devices for manipulating the temperature of a surface are generally provided herein. The present disclosure relates to a device that includes one or more heating and/or cooling elements, or other suitable thermal actuators placed near a surface, such as the skin of a user. The device may be configured to generate one or more (optionally alternating) thermal profiles at the surface, which may be accomplished by generating a series of thermal pulses in succession and/or essentially continuous or semi-continuous thermal input, which may vary over time. Such thermal profiles, when suitably applied, may result in an enhanced thermal sensation for a user which, in some cases, may provide the user with a more pleasurable thermal experience than would otherwise be the case without the generation of the thermal profiles. Advantageously, in some embodiments, one or more properties of each thermal profile may be adjusted in order to provide continuous or semi-continuous enhanced thermal sensation to the user. An thermal profile may include an average frequency, an oscillation window, and/or an average temperature, each of which may be adjustable. In some embodiments, the thermal profile (or one or more properties of the alternating thermal profile) may be adjusted in response to a signal sent to the device generated by a sensor and/or a user input. An alternating thermal profile may alternate in warming and cooling, frequency of pulses, rate of temperature change, or any other suitable property of the thermal profile, as the present disclosure is not so limited.

Without wishing to be bound by theory, a person's perception of temperature is a complex interaction of both absolute temperature, temperature difference relative to current skin temperature, and a rate of change of the temperature applied to the person's skin. Accordingly, when applying a thermal profile to a user that is intended to apply a thermal sensation, the applied thermal profile may include temperatures and rates of temperature change as detailed below. In one embodiment, the applied temperature may be greater than or equal to 20° C., 25° C., 30° C., 31° C., 35° C. and/or any other appropriate temperature. Correspondingly, the applied temperature may be less than or equal to 45° C., 40° C., 36° C., 35° C., 33° C., 30° C., 27° C., 25° C., 23° C. and/or any other appropriate temperature. Combinations of the above noted ranges are contemplated including, for example, temperatures applied to a user that are between or equal to 20° C. and 45° C., 20° C. and 40° C., 30° C. and 36° C., as well as 31° C. and 35° C. These temperature ranges may be combined with rates of temperature change applied to a user's skin that are greater than or equal to 0.01° C./s (Celsius per second), 0.05° C./s, 0.1° C./s, 0.2° C./s, 0.5° C./s, 1° C./s, 1.5° C./s, 2.5° C./s, 5° C./s, 7.5° C./s, 10° C./s, and/or any other appropriate rate of temperature change. Applied rates of temperature change may also be less than or equal to 10° C./s, 7.5° C./s, 5° C./s, 2.0° C./s, 1.75° C./s, 1.25° C./s, 0.75° C./s, 0.3° C./s, 0.15° C./s, 0.075° C./s, and/or any other appropriate rate of temperature change. Combinations of these rates of temperature change are contemplated including, for example, a rate of temperature change between or equal to 0.01° C./s and 2.0° C./s, 0.05° C./s and 1° C./s, 0.1° C./s and 0.3° C./s, 0.01° C./s and 0.1° C./s, 0.1° C./s and 10° C./s, as well as 0.5° C./s and 2° C./s with rates greater than about 0.1° C./s being generally associated with larger perceived subjective thermal sensations due to the rate sensitivity of a user's skin to changes in temperature. Of course, different combinations of the above described temperature ranges and rates of temperature change, as well as ranges both greater than and less than those noted above, are also contemplated as the present disclosure is not so limited. Additionally, it should be noted that device according to exemplary embodiments described herein may be employed to raise the temperature of an abutting surface from an initial surface temperature (i.e., heat) and/or may be employed to lower the temperature of an abutting surface from the initial surface temperature (i.e., cool), as the present disclosure is not so limited. Further, the thermal profiles applied to a surface, such as a user's skin, during use may provide only cooling, only heating, or both heating and cooling as the disclosure is not limited to any particular thermal profile.

The above noted temperature changes may be applied cyclically to a user. Accordingly, in some embodiments, the individual warmth and cooling portions of a thermal profile may be applied for various durations. For example, the individual portions (e.g., thermal pulses) of a thermal profile may be applied for durations greater than or equal to 0.25 seconds, 0.5 seconds, 1 second, 2 seconds, 5 seconds, 10 seconds, 15 seconds, 30 seconds, 1 minute, 2 minutes, 5 minutes, and/or any other appropriate time period. Correspondingly, the individual portions of thermal profile may be applied for durations less than or equal to 10 minutes, 5 minutes, 2 minutes, 1 minute, 30 seconds, 15 seconds, 10 seconds, 5 seconds, 3 seconds, 2 seconds, 1 second and/or any other appropriate duration. Combinations of the above ranges are contemplated including, for example, durations for the individual thermal periods that are between or equal to 2 seconds and 15 seconds, 0.5 seconds and 5 seconds, 30 seconds and 2 minutes, 30 seconds and 10 minutes, 1 second and 10 seconds, and/or any other appropriate combination. For example, instances in which a thermal actuator applies a thermal sensation during a user's inhalation or sucking action, an individual pulse and/or a series of pulses may be applied over a time duration that is less than about 30 seconds, 20 seconds, 10 seconds, and/or any other appropriate time period. Of course embodiments in which durations both greater than and less than those noted above are applied by a device for eliciting thermal sensations are also contemplated as the disclosure is not so limited.

The above noted rates of temperature change, as well as other rates of temperature change described herein, may either refer to an average rate of temperature change during a particular portion of a thermal profile when changing from a first temperature to a second temperature and/or they may refer to a temperature change rate that is applied during at least a portion of the applied thermal profile. For example, variable or constant temperature change rates may be applied when changing from a first temperature to a second temperature. Therefore, a particular rate may either be applied during at least a portion of the noted temperature change and/or the rate may correspond to an average rate during the noted temperature change.

In some embodiments, a face engaging device provides energy-efficient generation of warming or cooling sensations in form-factors using a low amount of power. Accordingly, when a device applies a desired thermal profile to an adjacent surface, the device may consume power during a warming or cooling portion of the thermal profile as detailed below. In one embodiment, the power consumed by applying a thermal profile during a warming or cooling portion of the thermal profile may be greater than or equal to 0.05 W, 0.1 W, 0.25 W, 0.5 W, 1 W, 2 W, 4 W, and/or are other appropriate power consumption. Correspondingly, the power consumed while applying a thermal profile may be less than or equal to 15 W, 10 W, 5 W, 3 W, 1 W, 0.75 W, 0.5 W, and/or any other appropriate power consumption. Combinations of the above noted ranges are contemplated including, for example, power consumption that is between or equal to 0.1 W and 1 W, 1 W and 5 W, 1 W and 10 W, 0.5 W and 4 W, as well as 1 W and 5 W, with a power consumption of 5 W or less being preferable in some embodiments. Of course, any suitable amount of power may be consumed by a device for eliciting thermal sensations, including powers both greater than and less than those noted above, as the present disclosure is not so limited.

According to exemplary embodiments described herein, a face engaging device housing may take any suitable shape for fitting into a mouth of a user or over a mouth or other portion of a face of a user. In some embodiments, the housing may be formed as a tube configured to be placed in the mouth of a user. In some embodiments, the housing may be formed as a flexible cone or other shape configured to be placed over the mouth and/or nose of a user. Of course, the housing of a face engaging device may take any suitable shape, as the present disclosure is not so limited.

According to exemplary embodiments described herein, the term "thermoelectric" is given its ordinary meaning in the art and refers to materials in which a temperature change is generated at a surface of the material upon application of an electric potential (e.g., voltage and corresponding current), in accordance with the thermoelectric effect (e.g., often referred to by other names such as the Peltier, Thomson, and Seebeck effects). Any suitable thermoelectric may be employed, a number of which are described further below. It should be understood that, while a portion of the description herein describes thermoelectric materials, the present disclosure is not limited to thermoelectric materials, and other thermal actuators may be employed where appropriate. For example, it can be appreciated that any suitable heating and/or cooling element may be employed; for example, a resistive heating device, convective thermal device, radiative thermal device, or any other suitable apparatus that is capable of generating a desired warming and/or cooling thermal sensation may be used.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1A is a schematic of one embodiment of a thermally controlled face engaging device 100 in use with a user 200. The face engaging device shown in FIG. 1A is configured as a nozzle of a vaporizer, a straw, or another device in which the user 200 fits the face engaging device into his or her mouth 202. According to the embodiment of FIG. 1A, the face engaging device includes a housing 102 including a fluid channel 104. In some embodiments as shown in FIG. 1A, the housing 102 is configured as a tube. The fluid channel may be configured to transport air, water, or another fluid that may be passed to and/or from the mouth 202 of the user 200. The face engaging device 100 also includes a plurality of thermal actuators 106 supported by the housing 102. Specifically, in the embodiment shown in FIG. 1A, the thermal actuators are disposed in the housing 102, where the thermal actuators are exposed to an exterior of the housing as well as the fluid channel. As will be discussed further with reference to FIG. 1B, such an arrangement may allow the thermal actuators to dissipate waste heat to the fluid channel 104 while a thermal profile is applied to lips 203 of the user. As shown in FIG. 1A, the face engaging device 100 also includes electrical connections 108 disposed in the housing that connect the thermal actuators 106 to a power supply such as a battery (not shown).

Figure 1B:
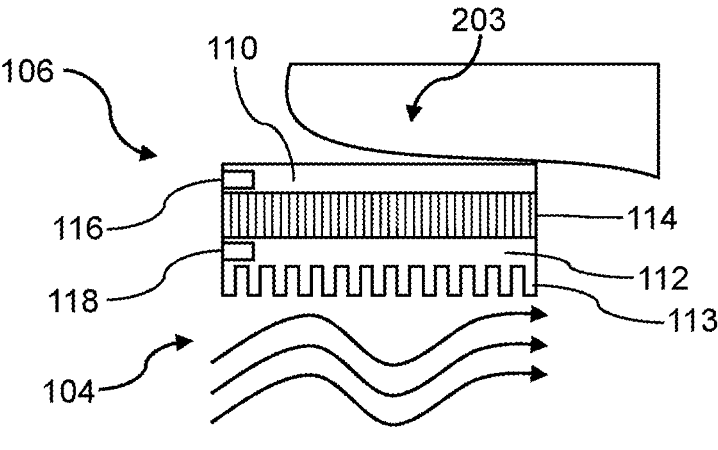
FIG. 1B is an enlarged schematic of section 1B of FIG. 1A.

FIG. 1B is an enlarged schematic of section 1B of FIG. 1A showing the arrangement of one of the thermal actuators 106 of the face engaging device 100. As shown in FIG. 1B, the thermal actuator is configured as a thermoelectric device. The thermal actuator includes a first exterior heat transfer surface 110 configured to be placed in contact with the user's skin and a second interior heat transfer surface 112 exposed to the fluid channel 104. Between the first heat transfer surface and the second heat transfer surface are thermoelectric piles 114 configured to apply a temperature profile at one of the first heat transfer surface and second heat transfer surface when a voltage is applied to the thermoelectric piles. For example, when a voltage is applied, the first heat transfer surface may be cooled and heat may flow to the second heat transfer surface. Such an arrangement may allow the thermal actuator to apply a cooling thermal profile to the lips 203 of the user. Likewise, the second heat transfer surface may be cooled and heat may flow to the first heat transfer surface when an opposite voltage is applied across the thermoelectric piles. Such an arrangement may allow the thermal actuator 106 to apply a heating and/or cooling thermal profile to the lips of the user. Accordingly, the thermal actuator of FIG. 1B may apply heating, cooling, or combinations of heating and cooling to a skin surface. As shown in FIG. 1B, the first heat transfer surface 110 includes a first temperature sensor 116, and the second heat transfer surface includes a second temperature sensor 118. The first and second temperature sensors may monitor the temperatures of the first and second heat transfer surface, respectively, so that an applied thermal profile may be controlled in a feedback control loop. Of course, while two temperature sensors are shown in FIG. 1B, any suitable number of temperature sensors located on any appropriate portion of the face engaging device may be used as the present disclosure is not so limited.

According to the embodiment shown in FIG. 1B, the thermal actuator 106 includes a plurality of fins 113 formed as a part of the second interior heat transfer surface 112. As noted previously, the thermal actuator 106 may be configured to transfer heat between the thermal actuator and the fluid in the fluid channel 104 formed in the housing of the face engaging device. For example, when a cooling thermal profile is generated at the first heat transfer surface and applied to the lips, waste heat may be transferred to the second, interior heat transfer surface 112. The fins 113 may be configured to enhance convective heat transfer relative to a second heat transfer surface that is flat or otherwise non-textured. The second heat transfer surface 112 and fins 113 may be configured so that waste heat is reliably transferred into fluid disposed in the fluid channel 104 when the thermal profile is applied. In some embodiments, a thermal profile may only be applied when fluid is flowing through the fluid channel, such that heat is drawn away from the second heat transfer surface into the flowing fluid. Of course, heat may be transferred into static fluid via the second heat transfer surface, as the present disclosure is not so limited. Additionally, while fins are employed in the embodiment of FIG. 1B, other texturing such as grooves, pins, etc. may be employed, or no texturing at all (i.e., a flat surface), as the present disclosure is not so limited. Also, while a cooling profile and transfer of heat into the fluid are discussed above, embodiments in which a heating profile is applied and heat is transferred from the fluid to the cooler heat transfer surface of an associated thermoelectric are also contemplated. Thus, it should be understood that the heat transfer surface may be used to transfer heat between the fluid and associated thermal actuator regardless of the specific type of thermal profile and/or thermal actuator used to maintain a desired operation of the device.

Figure 2:
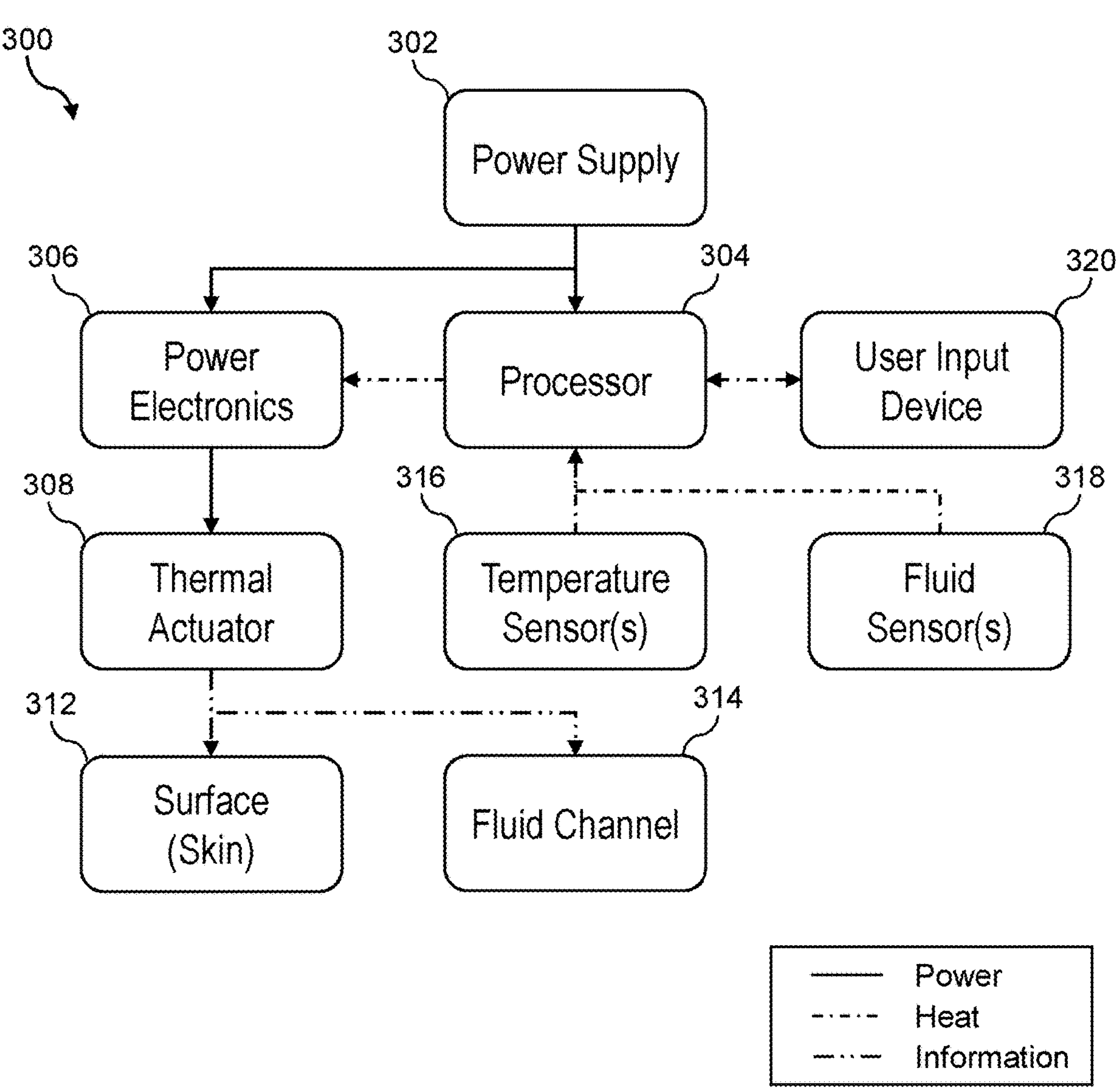
FIG. 2 is a block diagram of a thermally controlled face engaging device.

FIG. 2 is a block diagram of a thermally controlled face engaging device 300 showing the flow of power, heat, and information in the face engaging device. As shown in FIG. 2, the face engaging device includes a power supply 302, which may be a portable power supply such as a battery. In some embodiments, the power supply may be a wired power supply, as the present disclosure is not so limited. As shown in FIG. 2, the face engaging device 300 also includes a processor 304. The processor may be configured to execute processor readable instructions stored in memory. The processor may receive inputs and control other components of the face engaging device. The face engaging device 300 also includes power electronics which may control power flow to a thermal actuator 308. For the processor 304 may control the power electronics 306 to alter the amount of voltage and amperage delivered to the thermal actuator 308. As discussed above with reference to FIGS. 1A-1B, the thermal actuator 308 is configured to apply a thermal profile to a surface 312. The thermal actuator 308 is configured to transfer heat between fluid in a fluid channel 314 and the thermal actuator to allow for temperature regulation of the thermal actuator 308.

According to the embodiment of FIG. 2, the processor 304 is configured to receive inputs from a plurality of sensors 316, 318 and a user input device 320. In particular, temperature sensor(s) 316 provide temperature information regarding heat transfer surfaces and/or surface 312. In some embodiments, the processor 304 may employ the information from the temperature sensors for feedback control of a thermal profile. In some embodiments, the temperature sensor(s) may be employed to detect contact with a user's skin. For example, the sensor may detect a temperature change of a heat transfer surface in contact with the user's skin from an initial temperature towards an initial skin temperature of the user (e.g. a temperature between about 33.5° C. and 37° C. depending on the body portion. When such a temperature change is experienced in over a time period less than a predetermined time period, or other appropriate metric, the processor may initiate operation of the system as described here. Of course, information from the temperature sensor(s) may be employed for any suitable purpose by the processor 304, as the present disclosure is not so limited. As shown in FIG. 2, the face engaging device may also include one or more fluid sensor(s) 318. The fluid sensor(s) may be configured as a flow sensor, pressure sensors, or other suitable sensors for providing information regarding the fluid in the fluid channel 314. For example, the fluid sensor may detect active flow through the fluid channel. The fluid sensor may also detect a pressure differential relative to environmental pressure, absolute pressure that is below a predetermined threshold, a pressure differential from a baseline or equilibrium pressure value, a pressure differential relative to an initial sensed pressure, and/or any other appropriate metric. The information from the fluid sensor(s) may also be employed as a trigger for applying a thermal profile to the surface 312. For example, when a pressure, pressure differential, flow velocity, volumetric flow rate, or other appropriate parameters meets a predetermined threshold the processor may initiate operation of the device. The user input device 320 may also be configured to receive input from a user. For example, the user input device may be a button, switch, dial, graphical user interface, or other arrangement for receiving input from a user. Information from the user input device may also be used as a trigger to apply a thermal profile to the surface 312. In one such embodiment, activation of a button or switch may be used to initiate operation of the device to apply a thermal profile to the surface 312. In some embodiments, input at the user input device may be employed to change one or more parameters of a thermal profile applied to the surface 312. For example, a duration, frequency, maximum temperature, temperature change rate, type of thermal profile, and/or other appropriate parameter may be selected and/or adjusted by a user via the user input device 320.

In some embodiments, a face engaging device 300 may not include a processor 304. Rather, the user input device and/or one or more sensors may be employed as a trigger to active the power electronics 306 to apply a thermal profile to the surface 312. In this manner, the system may be analog and the power electronics may be activated when a predetermined threshold is met. Such an arrangement may be beneficial for user activated devices (e.g., vaporizers, inhalers, etc.) where feedback control and/or execution of computer readable instructions is not desirable and/or too power intensive. Of course, any suitable control scheme may be employed for a face engaging device, including analog and digital open loop or closed-loop control schemes, as the present disclosure is not so limited.

Figure 3:
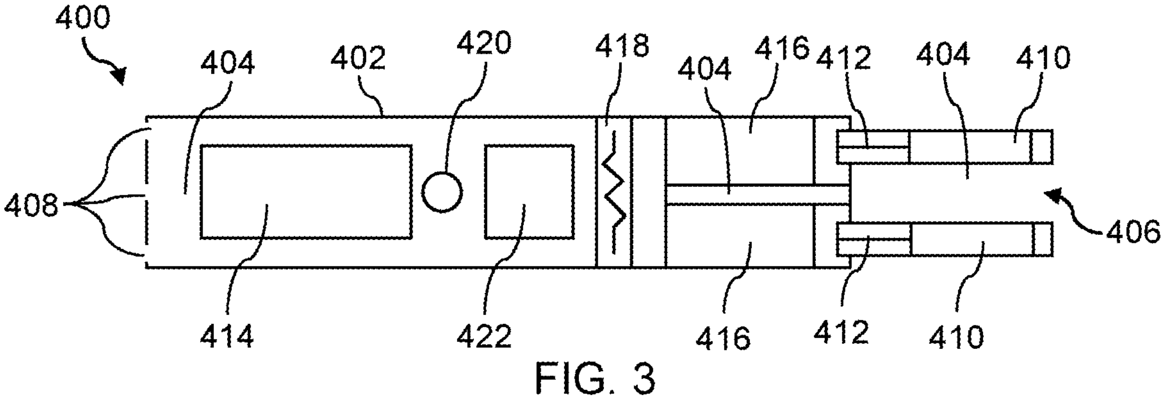
FIG. 3 is a schematic of one embodiment of a vaporizer including a thermally controlled face engaging device.

FIG. 3 is a schematic of one embodiment of a vaporizer 400 including a thermally controlled face engaging device. As shown in FIG. 3, the vaporizer includes a housing 402 having an internal fluid channel 404. The fluid channel terminates in an opening 406 on a first end portion of the housing 402, and in a plurality of inlets 408 on a second end portion of the housing opposite the first end or any other appropriate portion of the housing distanced from the opening on the first end portion. According to the embodiment of FIG. 3, the vaporizer is configured to pass air from the environment through the inlets 408, through the fluid channel 404, and out of the opening 406 into the mouth of a user. The movement of air through the fluid channel may be generated by the inhalation of a user, who generates a pressure differential between the mouth and/or lungs and the external environment to draw fluid into the fluid channel 404. However, embodiments in which the flow of fluid through the channel is at least partially due to the transport of a pressurized fluid from a canister or other pressure source in fluid communication with the channel are also contemplated. As shown in FIG. 3, the vaporizer 400 includes one or more thermal actuators 410, in this case two, positioned adjacent to the opening 406. The one or more thermal actuators may be positioned such that they may be placed in contact with a user's lips, or other portion of a user's face, during use. In the embodiment of FIG. 3, the thermal actuators may be configured as thermoelectric devices, with a first heat transfer surface disposed on an exterior of the housing 402 and a second heat transfer surface exposed to the fluid channel 404. The thermal actuators may be configured to apply a thermal profile to the skin (e.g., lips) of a user when the vaporizer is placed in the mouth of the user. As shown in FIG. 3, the thermal actuators are connected to a battery 414 with electrical connections 412 disposed in the housing 402.

According to the embodiment of FIG. 3, the vaporizer 400 also includes a liquid reservoir 416 that includes a liquid configured to be vaporized and entrained in air flowing through the fluid channel 404. As shown in FIG. 3, the vaporizer includes a liquid heater 418 configured to heat liquid from the liquid reservoir 416. The heater may vaporize the liquid and/or an active chemical agent contained in the fluid. As air is drawn through the fluid channel 404, the vaporized material may be entrained in the flow and delivered to the user through the opening 406. According to the embodiment of FIG. 3, the vaporizer also includes a pressure sensor 420 and a user input device 422. The pressure sensor may be configured to detect a differential pressure between the fluid channel 404 and the environment, an absolute pressure of the fluid channel, a differential pressure between the fluid channel and a baseline or equilibrium pressure value, and/or a pressure differential relative to an initial sensed pressure. Such a pressure may be indicative of air flowing through the fluid channel 404. When the absolute pressure and/or differential pressure reaches a predetermined threshold, the liquid heater 418 and thermal actuators 410 may be activated. The user input device 422 may be configured as a graphical user interface with which a user may monitor a vaporization process and/or alter one or more parameters of a thermal profile applied to the lips of the user by the thermal actuator 410. Of course, in some embodiments the user input device 422 may be configured as a button or another suitable input device to receive input from a user, as the present disclosure is not so limited.

Figure 4:
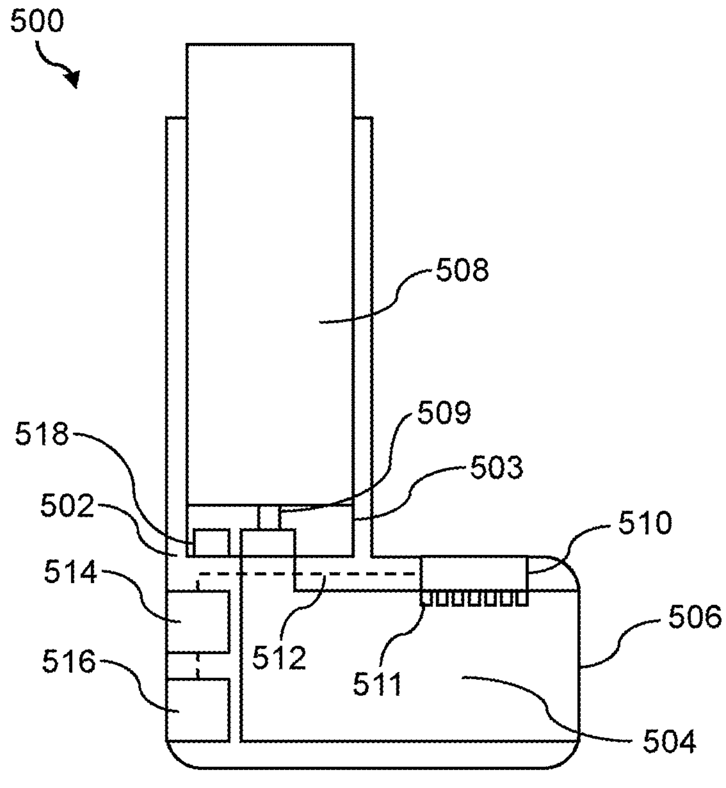
FIG. 4 is a schematic of one embodiment of an inhaler including a thermally controlled face engaging device.

FIG. 4 is a schematic of one embodiment of an inhaler 500 including a thermally controlled face engaging device. As shown in FIG. 4, the inhaler includes a housing 502 having a fluid channel 504. The housing also includes a cylinder receptacle 503 configured to receive and support a cylinder 508 which in some embodiments may be a pressurized cylinder including a compound to be delivered to a user. In contrast to the embodiment of FIG. 3, the inhaler of FIG. 4 may not include air inlets into the fluid channel 504. Instead, the fluid channel 504 is connected at one end to the cylinder 508 which may include a pressurized propellant in addition to a powder, gas, and/or fluid within the cylinder at a first portion of the channel and terminates at a second portion of the inhaler at an opening 506 formed in portion of the inhaler configured to be placed in fluid communication with a mouth of a user. While an inhaler without inlet flow paths from an exterior environment is shown in the figure, instances in which fluid channels extend around or past the cylinder and/or separate inlets from an exterior environment to the channel are formed in the inhaler between the cylinder and the opening are also contemplated. In either case, when the cylinder is depressed, a metering valve 509, or other actuator, may provide a supply of gas which may include an entrained powder, other gas, or fluid from the cylinder into the fluid channel 504. The flow of gas may then be inhaled by a user when their mouth is in fluid communication with the opening 506.

According to the embodiment of FIG. 4, the inhaler includes a thermal actuator 510 supported by the housing 502. The thermal actuator is configured to apply a thermal profile to the skin (e.g., lips) of the user when the mouth is placed in fluid communication with the opening 506. As shown in FIG. 4, the inhaler includes a plurality of fins 511 configured to enhance convective heat transfer of heat between the thermal actuator and the flow of fluid within the fluid channel relative to a smooth or non-textured heat transfer surface with less surface area. The thermal actuator 510 may be connected to a processor 514 and battery 516 via an electrical connection 512 disposed in the housing 502. As discussed previously, the processor 514 may be configured to control power delivery to the thermal actuator to control the application of a thermal profile to a user's skin. According to the embodiment of FIG. 4, the inhaler may also include a microswitch 518 configured to be depressed when the cylinder is actuated to supply gas to the fluid channel. The activated state of the switch may trigger the application of a thermal profile by the thermal actuator. The microswitch may be electrically connected to the processor and/or battery 516 so as to wake or power the processor and/or thermal actuator 510. In this manner, the application of a thermal profile may be based on the manual actuation of the cylinder 508 by a user. Of course, embodiments in which operation of the device is controlled using such a switch without the use of a separate processor are also contemplated.

Figure 5:
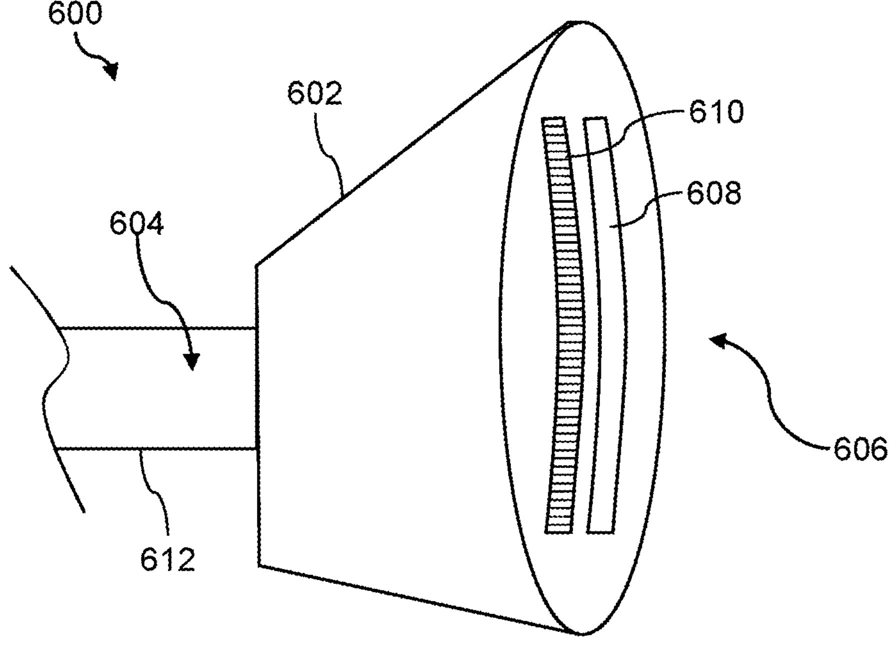
FIG. 5 is a schematic of one embodiment of a facemask including a thermally controlled face engaging device.

FIG. 5 is a schematic of one embodiment of a facemask 600 including a thermally controlled face engaging device. According to the embodiment of FIG. 5, the facemask may be an air or oxygen supply mask that may be commonly employed in aircraft, medical, scuba, or other applications. As shown in FIG. 5, the facemask includes a housing 602 which is configured to fit over the face of a user. The housing 602 includes a fluid channel 604 terminating in an opening 606 that is correspondingly configured to be placed in fluid communication with the mouth and/or nose of the user. On an internal surface of the housing 602 are a first heat transfer surface 608 and a second heat transfer surface 610. The first heat transfer surface may be configured to be placed in contact with the skin of the user (e.g., face around the mouth and nose) when the device is worn by a user. The second heat transfer surface 610 is configured to be exposed to the fluid channel 604 and not in contact with the skin of the user when the device is worn. The first heat transfer surface is configured to apply a thermal profile to the skin of the user, and the second heat transfer surface is configured to transfer heat between the thermal device and a flow of fluid through the fluid channel 604. That is, the first and second heat transfer surfaces may be coupled to a thermal actuator configured to thermally regulate a temperature of a user's skin in contact with the first heat transfer surface and transferring heat between the second heat transfer surface 610 and fluid disposed in the fluid channel. In some embodiments, the second heat transfer surface maybe textured, for example, with pins, grooves, or fins, to enhance convective heat transfer relative to a smooth heat transfer surface. As shown in FIG. 5, the housing 602 is coupled to a fluid supply tube 612 which may be coupled to another fluid source (e.g., pressurized gas container) which supplies a flow of fluid through the fluid channel 604.

FIGS. 6A-9B depict various embodiments of thermally controlled face engaging devices 700 having different shapes and sizes of heat transfer surfaces 706 exposed to the mouth of a user. In particular, the face engaging devices of FIGS. 6A-9B are configured as nozzles configured to be placed in the mouth of the user, where the heat transfer surfaces are configured to contact the lips of the user. Each set of figures depicts a first side of the face engaging device and a second opposite side of the face engaging device.

Figures 6A, 6B, 7A, 7B, 8A, 8B, 9A, 9B:
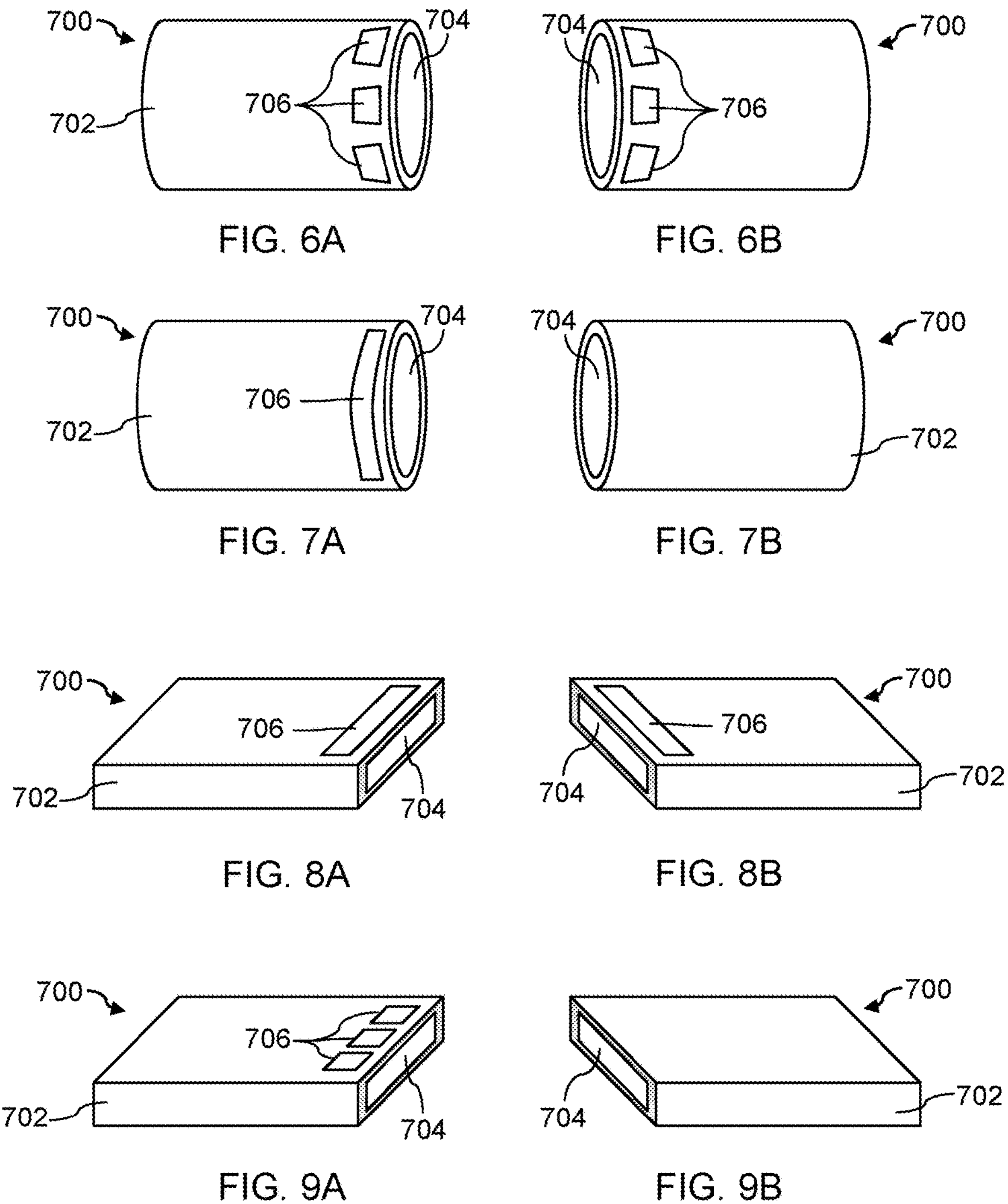
FIG. 6A is a top perspective view of another embodiment of a thermally controlled face engaging device.
FIG. 6B is a bottom perspective view of the thermally controlled face engaging device of FIG. 6A.
FIG. 7A is a top perspective view of another embodiment of a thermally controlled face engaging device.
FIG. 7B is a bottom perspective view of the thermally controlled face engaging device of FIG. 7A.
FIG. 8A is a top perspective view of another embodiment of a thermally controlled face engaging device.
FIG. 8B is a bottom perspective view of the thermally controlled face engaging device of FIG. 8A.
FIG. 9A is a top perspective view of another embodiment of a thermally controlled face engaging device.
FIG. 9B is a bottom perspective view of the thermally controlled face engaging device of FIG. 9A.

According to the embodiment of FIGS. 6A-6B, the face engaging device 700 includes a housing 702 supporting three heat transfer surfaces 706 on both the first side (FIG. 6A) and the second side (FIG. 6B) of the device. In particular, the heat transfer surfaces are arranged circumferentially and symmetrically around the housing 702. The separate heat transfer surfaces may be thermally coupled with one or more thermal actuators including, for example, a separate thermal actuator associated with each heat transfer surface. The housing 702 is configured as a cylindrical tube including a cylindrical fluid channel 704.

According to the embodiment of FIGS. 7A-7B, the face engaging device 700 includes a housing 702 supporting a single heat transfer surface 706 on only the first side (FIG. 7A) of the device. The heat transfer surface extends along a single arc of the housing 702, where the heat transfer surface spans an arc between approximately 30 degrees and 180 degrees. Like the embodiment of FIGS. 6A-6B, the housing 702 is configured as a cylindrical tube including a cylindrical fluid channel 704. In some embodiments, the heat transfer surface may extend along an arc of the housing up to 360 degrees, as the present disclosure is not so limited.

According to the embodiment of FIGS. 8A-8B, the face engaging device 700 includes a housing 702 supporting a single heat transfer surface 706 on the first side (FIG. 8A) and a single heat transfer surface 706 on the second, opposite side (FIG. 8B) of the device. The heat transfer surface on both sides extends along a width of the housing 702. The housing 702 of FIGS. 8A-8B, is configured as a rectangular (e.g., box) tube including a correspondingly shaped fluid channel 704. Again, the separate heat transfer surfaces may be thermally coupled with one or more thermal actuators.

According to the embodiment of FIGS. 9A-9B, the face engaging device 700 includes a housing 702 supporting a plurality (e.g., three) heat transfer surfaces 706 on the first side (FIG. 8A) of the device. The heat transfer surfaces form multiple square surfaces that are distanced from one another. Again, the separate heat transfer surfaces may be thermally coupled with one or more thermal actuators. Like the housing of FIGS. 8A-8B, the housing 702 of FIGS. 9A-9B, is configured as a rectangular (e.g., box) tube including a correspondingly shaped fluid channel 704.

Figures 10, 11, 12:
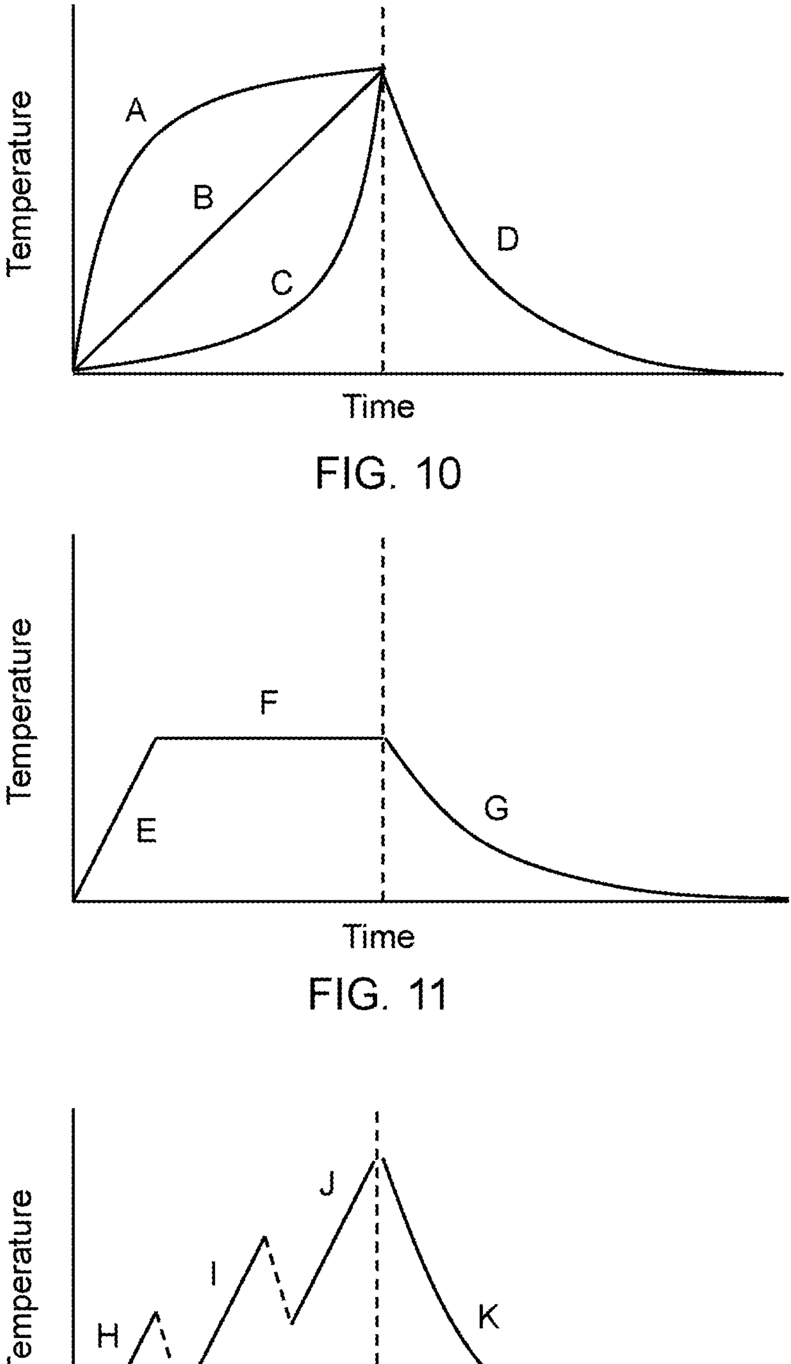
FIG. 10 is a graph of some embodiments of a temperature profile applied by a thermally controlled face engaging device.
FIG. 11 is a graph of another embodiment of a temperature profile applied by a thermally controlled face engaging device.
FIG. 12 is a graph of another embodiment of a temperature profile applied by a thermally controlled face engaging device.

FIGS. 10-12 depict various embodiments of thermal profiles that may be applied by a face engaging device. While certain thermal profiles are shown and described herein, any suitable heating, cooling, or heating and cooling profile may be applied by a thermal actuator of a face engaging device, as the present disclosure is not so limited.

FIG. 10 is a graph of some embodiments of a temperature profile applied by a thermally controlled face engaging device, where the temperature profile is monotonically increasing during a first portion of an actuation cycle. According to FIG. 10, the thermal profiles may be heating thermal profiles, where the initial temperature is lower than the final or set point temperature. In profile A, the temperature may be raised as an increasing exponential decay function. In profile B, the temperature is raised linearly. In profile C, the temperature is raised exponentially. Once the temperature is raised to a predetermined set point (as shown by the dashed line), the thermal actuator may be deactivated. When unpowered, the temperature may exponentially decay toward the initial temperature, as shown by profile D. In some embodiments, a thermal profile may include a plurality of thermal pulses, where each pulse includes a monotonically applied profile followed by a rest period of exponential decay or other appropriate profile towards the initial temperature of the device. Such an embodiment will be discussed further with reference to FIG. 12. While a warming profile is depicted in the figure, in some embodiments, a thermal profile may be a monotonically decreasing cooling thermal profile. That is, opposite to the thermal profile of FIG. 10, the initial temperature may be higher than the final or set point temperature though the overall profile shape and operation may be similar to that shown in the figure but for cooling.

FIG. 11 is a graph of a rise and hold temperature profile applied by a thermally controlled face engaging device. As shown in FIG. 11, profile E includes a monotonically increasing temperature, where the profile is linear. Of course, other monotonically increasing temperature profiles may be applied as shown in FIG. 10, as the present disclosure is not so limited. In profile F, a temperature set point is maintained. After a predetermined amount of time, the thermal actuator may be deactivated, where the temperature then exponentially decays (e.g., relaxes) or is otherwise permitted to return back towards an initial temperature. Such a profile may be appropriate where an initial rapid change in temperature is desirable to enhance a thermal sensation applied to a user while limiting the overall temperature change. For instance, it may be desirable to provide thermal stimulation during a long inhalation by a user using a particular device. In some embodiments, the overall profile of FIG. 11 may be inversed so that the profile is a decline and hold rather than a rise and hold where a cooling profile is desirable.

FIG. 12 is a graph of another embodiment of a temperature profile applied by a thermally controlled face engaging device where the thermal profile includes a plurality of thermal pulses. During each of the profiles H, I, and J, a linear profile, or other appropriate type of profile, is applied to control an increase in the applied temperature. The increased temperature may be followed by a relaxation period back toward the initial temperature where the pulse started. However, the temperature does not relax fully to the initial temperature. Accordingly, after each thermal pulse the temperature is higher than the maximum temperature of the prior pulse. Such an arrangement may be beneficial to mitigate the effects of thermal adaptation in a user. Once a predetermined number of thermal pulses are applied, and/or a maximum temperature change is reached, the temperature may be allowed to return towards the initial temperature as shown by profile K. In some embodiments, the overall profile of FIG. 12 may be inversed such that a plurality of cooling pulses is applied to the user as opposed to a plurality of heating pulses. In some embodiments, heating and cooling pulses may be alternated or otherwise combined to elicit a particular thermal sensation. In some embodiments, the relaxation period for a temperature profile may be actively powered, such that a thermal actuator controls the relaxation of the device temperature back towards the initial temperature.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A face engaging device comprising:

a housing including a fluid channel extending through at least a portion of the housing to an opening configured to be placed in fluid communication with a mouth and/or nose of a user, wherein the housing includes a first surface configured to be placed in contact with skin of a user and a second surface exposed to the fluid channel; and a thermal actuator supported by the housing and including a first heat transfer surface positioned on the first surface, wherein the first heat transfer surface is configured to be in contact with the skin of the user when the opening is placed in fluid communication with the mouth and/or nose of the user, wherein the thermal actuator includes a second heat transfer surface positioned on the second surface.

2. The face engaging device of claim 1, wherein the first surface is an exterior surface of the housing, and the second surface is an interior surface of the housing exposed to the fluid channel.

3. The face engaging device of claim 1, wherein the thermal actuator is a thermoelectric actuator, and wherein the second heat transfer surface includes at least one selected from the group of pins or fins configured to provide convective heat transfer between the thermoelectric actuator and the fluid disposed in the fluid channel.

4. The face engaging device of claim 1, further comprising an inlet connected to the fluid channel at a portion of the housing distanced from the opening, wherein the inlet is configured to allow fluid to flow from an external environment into the fluid channel in response to a pressure differential generated between the mouth and/or nose of the user and the external environment.

5. The face engaging device of claim 4, further comprising:

a liquid reservoir disposed in the housing containing a liquid; and a liquid heating element configured to selectively vaporize the liquid in the liquid reservoir into the fluid channel.

6. The face engaging device of claim 4, further comprising a pressure sensor configured to detect a change in pressure and/or an absolute pressure, wherein the thermal actuator is configured to apply a thermal profile to the skin of the user in response to the change in pressure and/or absolute pressure reaching a threshold.

7. The face engaging device of claim 1, further comprising a selectively actuatable container configured to eject a fluid into the fluid channel, wherein the thermal actuator is configured to apply a thermal profile to the skin of the user in response to actuation of the container.

8. The face engaging device of claim 1, further comprising a temperature sensor configured to detect the temperature of the first heat transfer surface.

9. The face engaging device of claim 8, wherein the temperature sensor is configured to control the thermal actuator to apply a thermal profile to the skin of the user based at least in part on the detected temperature.

10. The face engaging device of claim 1, wherein a thermal profile applied to the skin by the thermal actuator includes at least one selected from the group of monotonically increasing, rise and hold, and a plurality of thermal pulses applied in succession.

11. The face engaging device of claim 1, wherein the thermal actuator is configured to apply a thermal profile to the skin of the user when the opening is placed in fluid communication with the mouth and/or nose of the user, and wherein the thermal actuator is configured to transfer heat between the thermal actuator and fluid disposed in the fluid channel.

12. The face engaging device of claim 11, further comprising a temperature sensor configured to detect a temperature of at least one side of the thermal actuator.

13. The face engaging device of claim 12, wherein the temperature sensor is configured to control the thermal actuator to apply the thermal profile to the skin of the user based at least in part on the detected temperature.

14. A method of operating a face engaging device including a thermal actuator, the method comprising:

placing an opening of a housing of the face engaging device in fluid communication with a mouth and/or nose of a user, wherein the opening is connected to a fluid channel extending through the housing;

positioning a first surface of the housing in contact with skin of the user and positioning a second surface of the housing to be exposed to the fluid channel;

applying a thermal profile to the skin of the user with the thermal actuator supported by the housing when the opening is placed in fluid communication with the mouth and/or nose of the user, wherein the thermal actuator includes a first heat transfer surface positioned on the first surface of the housing and a second heat transfer surface positioned on the second surface of the housing;

drawing fluid through the fluid channel and into the mouth and/or nose of the user; and transferring heat between the thermal actuator and the fluid passing through the fluid channel.

15. The method of claim 14, wherein transferring heat from the thermal actuator to the fluid passing through the fluid channel includes transferring the heat through convection via at least one selected from the group of pins, fins, texturing, and a heat spreader.

16. The method of claim 14, wherein drawing fluid through the fluid channel includes generating a differential pressure between the mouth and/or nose of the user and a baseline pressure, wherein the fluid flows through an inlet connected to the fluid channel at a portion of the housing distanced from the opening.

17. The method of claim 16, further comprising vaporizing liquid contained in a liquid reservoir disposed in the housing into the fluid channel.

18. The method of claim 16, further comprising detecting a change in pressure and/or an absolute pressure sensor reaching a threshold.

19. The method of claim 18, wherein the thermal profile is applied in response to the change in pressure and/or absolute pressure reaching the threshold.

20. The method of claim 14, further comprising ejecting a fluid into the fluid channel, wherein the thermal profile is applied when the fluid is ejected into the fluid channel.

21. The method of claim 14, further comprising detecting a temperature of at least one side of the thermal actuator.

22. The method of claim 14, wherein the thermal profile includes at least one selected from the group of monotonically increasing and rise and hold.

23. The method of claim 14, wherein the thermal profile includes a plurality of thermal pulses applied in succession.

24. The method of claim 14, wherein the thermal actuator is a thermoelectric actuator.

* * * * *